United States Patent [19]

Walraevens et al.

[11] Patent Number: 4,675,131

[45] Date of Patent: Jun. 23, 1987

[54] ORGANIC QUATERNARY AMMONIUM COMPOUNDS AND PROCESS FOR THE PREPARATION THEREOF

[75] Inventors: René Walraevens; Jean-Marc Coisne, both of Brussels, Belgium

[73] Assignee: Interox(Société Anonyme), Brussels, Belgium

[21] Appl. No.: 807,785

[22] Filed: Dec. 11, 1985

[30] Foreign Application Priority Data

Dec. 12, 1984 [FR] France ............................. 84 19110

[51] Int. Cl.$^4$ .................. C07C 93/16; C07C 85/00
[52] U.S. Cl. ................................. 260/404; 260/410; 560/251; 560/252
[58] Field of Search ............... 260/404, 410; 560/251, 560/252

[56] References Cited

U.S. PATENT DOCUMENTS

| 4,368,127 | 1/1983 | Richmond | 560/252 |
| 4,409,209 | 10/1983 | Richmond | 560/252 |
| 4,456,554 | 6/1984 | Walz et al. | 260/403 |

FOREIGN PATENT DOCUMENTS

| 0021546 | 1/1981 | European Pat. Off. | 560/252 |
| 0075168A1 | 9/1982 | European Pat. Off. | 260/404 |
| 2430140 | 2/1986 | Fed. Rep. of Germany | 560/251 |
| 2092921 | 1/1972 | France | 260/404 |

OTHER PUBLICATIONS

Kunitake et al, J. Am. Chem. Soc. 1984, vol. 106, No. 7, Bilayer Membranes of Triple-Chain Ammonium Amphiphiles.
Yoshino et al, Bulletin of the Chemical Society of Japan, vol. 47(2), 405-409 (1974), Synthetic Studies by the Use of Carbonates. I. The Nucleophilic Substitution Reaction of Ethylene Carbonate with Amine Hydrohalides.
B. Prager and P. Jacobson, Beilstein, vol. IV, 1922 Berlin, Aminoderivate der Dioxy-Verbindungen, pp. 301-303.

Primary Examiner—Werren B. Lone
Attorney, Agent, or Firm—Spencer & Frank

[57] ABSTRACT

Quaternary ammonium compounds having the general formula:

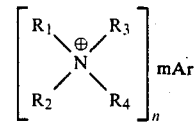

in which,
R$_1$ is an alkyl or aryl group, unsubstituted or substituted by at least two ester groups;
R$_2$, R$_3$ and R$_4$ are alkyl, aryl, aryl alkyl or alkyl aryl groups substituted by ester groups comprising no more than 10 carbon atoms;
m, r and n are whole numbers;
A$^{r-}$ is an anion such that $m \times r = n$. The compounds are obtained by treatment of a tert.alcohol-amine with an alkylating or arylating agent and an acylating agent. They may be used as activators of persalts in wash compositions.

18 Claims, No Drawings

ORGANIC QUATERNARY AMMONIUM COMPOUNDS AND PROCESS FOR THE PREPARATION THEREOF

The present invention relates to organic quaternary ammonium compounds having a plurality of ester functions.

Trimethyl-(2,3-diacetoxypropyl)-ammonium chloride which is an organic quaternary ammonium compound having two ester functions on a single alkyl group is well known (Beilstein, vol.IV, 1922 Berlin, B. Prager and P. Jacobson "Aminoderivate der Dioxy-Verbindungen" pages 301 to 303, * page 302 line 45 to line 48 *).

The purpose of the invention is to provide new organic compounds having a quaterny ammonium function where at least three of the groups connected to the nitrogen atom are substituted by ester groups.

The quaternary ammonium compounds according to the invention are compounds having the general formula:

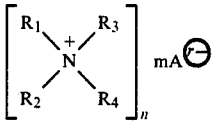

in which, $R_1$ represents an alkyl, aryl, aryl alkyl or alkyl aryl group, unsubstituted or substituted by at least two ester groups;

$R_2$, $R_3$ and $R_4$ represent alkyl, aryl, aryl alkyl, alkyl aryl groups, each substituted by at least one ester group having the formula:

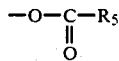

in which $R_5$ represents an alkyl, aryl, aryl alkyl or alkyl aryl group comprising 1 to 9 carbon atoms;

$A^\ominus$ represents an organic or inorganic anion;

n and r are whole numbers;

m is a whole number with the value 1, 2 or 3 and such that $m \times r = n$.

In the compounds according to the invention, the alkyl groups are any branched or unbranched aliphatic chains, any cycloalkyl radicals or any aliphatic chains substituted by a cycloalkyl radical, possibly substituted, such as straight or branched chains of 1 to 20 carbon atoms such as the methyl, propyl, isopropyl, n-butyl, isobutyl, sec.butyl and tert.butyl, n-pentyl, 1-methylbutyl, 2-methylbutyl, 3-methylbutyl, 1-ethylpropyl, 1,1-dimethylpropyl, 2,2-dimethylpropyl groups, n-hexyl and its branched isomers, n-heptyl, n-octyl, n-nonyl, n-decyl, n-undecyl, n-dodecyl groups and their branched isomers, cyclopropyl, cyclopentyl and cyclohexyl groups and the groups mentioned having one or more unsaturations.

The aryl groups are any monocyclic or polycyclic aromatic derivative, possibly substituted, such as the phenyl, 2,3-xylyl, 2,4-xylyl, 2,5-xylyl, 2-tolyl, 3-tolyl, 4-tolyl, mesityl, o-cumenyl, m-cumenyl, p-cumenyl, 1-naphthyl, 2-naphthyl, 1-anthryl, 2-anthryl, 1-phenanthryl, 2-phenanthryl 2-chrysyl and 2-pyryl groups.

The alkyl aryl groups are any aryl group substituted by one or more saturated or unsaturated groups such as the alkyl benzyl, alkyl naphthyl and alkyl anthryl groups.

The aryl alkyl groups are any alkyl groups substituted by one or more aryl groups such as the benzyl, phentyl and trityl groups.

Inorganic or organic anion means any anion originating from an inorganic or organic acid such as the anions chloride, bromide, iodide, fluoride, sulphate, hydrogen sulphate, carbonate, bicarbonate, phosphate, monohydrogen phosphate, dihydrogen phosphate, pyrophosphate, metaphosphate, thiosulphate, nitrate, methosulphate, dodecyl sulphate, dodecylbenzene sulphonate, phosphonate, methyl phosphonate, methane disulphonate, methyl sulphonate, ethane sulphonate, 1,2-ethanedisulphonate.

In the compounds according to the invention, the $R_2$, $R_3$ and $R_4$ groups are each substituted by at least one ester group. The latter may be derived from any monocarboxylic or polycarboxylic acid such as acetic, propionic, butanoic, octanoic, nonanoic and decanoic acid. Suitable compounds are those in which the aliphatic ester groups are straight chained or branched and in which the $R_5$ group comprises 7 to 9 carbon atoms, such as the methyltris(2-octyloxyethyl)-ammonium chlorides. The two groups $R_3$ and $R_4$ may have equal or different numbers of ester groups. Especially well suitable compounds are those in which the $R_5$ group contains less than 7 carbon atoms and, preferably less than 4 atoms. Most advantageous compounds are those in which the $R_5$ group contains only one carbon atom.

Compounds according to the invention include those in which the $R_1$ group is unsubstituted such as methyl-tris (2-acetoxyethyl)-ammonium salts, particularly methyl-tris (2-acetoxyethyl)-ammonium methosulphate, methyl-tris (2-acetoxyethyl)-ammonium dodecylsulphate, methyl-tris (2-acetoxyethyl)-ammonium dodecylbenzenesulphonate, and methyl-tris(2-acetoxyethyl)-ammonium chloride.

Compounds especially advantageous according to the invention are those in which the group $R_1$ is unsubstituted and in which at least one of the $R_2$, $R_3$ or $R_4$ groups comprises two acetic ester groups, such as for example n-butyl-tris(2,3-diacetoxypropyl)-ammonium chloride.

Preferred compounds according to the invention are those in which the $R_1$ group is substituted by at least two ester groups, particularly (2,3-diacetoxypropyl)-tris(2-acetoxyethyl)-ammonium chloride.

The invention also relates to a process for the preparation of the compounds according to the invention according to which a tert.amine having an alcohol group on each group connected to the nitrogen is treated with an alkylating or arylating agent and with an acylating agent chosen from acyl anhydrides and acyl chlorides.

In the process according to the invention, the tert.amine containing an alcohol group is any tert.amine in which the groups connected directly to the nitrogen atom are aliphatic or aromatic groups containing an alcohol group. Triethanolamine, tris(2,3-dihydroxypropyl)amine, tris(2-hydroxypropyl)-amine, methyl-bis(2,3-dihydroxypropyl)amine, N,N-diethanol-aniline are examples of suitable amines. Triethanolamine is preferred.

The alkylating or arylating agent can be any alkyl, alkyl aryl or aryl alkyl salt capable of bringing about quaternisation of the amine. It can, for example, be chosen from alkyl, aryl and alkyl aryl halides and sulphates, such as dimethylsulphate, the chlorides bromides and iodides of mthyl, ethyl or benzyl, methyldodecylbenzene sulphate or from the halohydroxyalkyls or halohydroxyaryls such as 2-bromoethanol, 1-chloro-2,3-propanediol and 2-chloro-3-phenyl-propan-1-ol.

The acylating agent can be any compound capable of bringing about esterification of at least two alcohol groups and is chosen from the acyl anhydrides and acyl chlorides such as acetic anhydride benzoic anhydride phthalic anhydride acetyl chloride and propionyl chloride.

In the process according to the invention, it is generally advisable that the treatment with the alkylating agent and the treatment with the acylating agent should not be simultaneous. The treatment with the alkylating agent can equally precede or follow the treatment with the acylating agent.

The quaternary ammonium compounds according to the invention have surfactant properties and an ability to react with hydrogen peroxide in an aqueous medium to form the corresponding peracids by perhydrolysis of the ester groups. Because of this, they find applications in the detergent industry where they constitute additives for detergent compositions in which they act as activators of persalts for low temperature washing.

Particular characteristics of the invention will be deduced from the following examples which describe processes for the preparation of compounds according to the invention.

EXAMPLE 1

Preparation of methyl-tris(2-acetoxyethyl)-ammonium methosulphate

A mixture of 29.8 g (0.2 mole) of triethanolamine, 78.5 g (1 mole) of acetyl chloride and 500 ml of chloroform was kept under reflux for 8 hours, after which period the gaseous release of hydrochloric acid ceased.

After cooling, the mixture was filtered and the filtrate was evaporated under a pressure of 2.67 kPa at 50° C. The resulting oily residue was then mixed with 25 g of sodium hydroxide in powder form and 250 ml of dry diethylether after which the mixture was filtered. The filtrate was then evaporated under a pressure of 2.67 kPa at 50° C. and the residue was distilled under reduced pressure (133 to 200 Pa). Boiling point established itself under these conditions at 145° to 146° C. 35.2 g (128 mmoles) of tris(2-acetoxy ethyl)amine were collected.

The tris(2-acetoxyethyl)-amine thus obtained was mixed with 17.9 g (142 mmoles) of dimethylsulphate and the mixture was kept at 40° C. for 2 hours. After cooling, the solid formed was suspended in 500 ml of diethylether, filtered and dried at 20° C. under a pressure of 1.33 kPa.

A quantity of 51 g of methyl-tris(2-acetoxyethyl)-ammonium methosulphate were obtained (yield: 64%).

EXAMPLE 2

Preparation of tris(2-acetoxyethyl)-(2,3-diacetoxypropyl)ammonium chloride

1st stage: synthesis of tris(2-hydroxyethyl)-2,3-dihydroxy propyl ammonium chloride A quantity of 44.8 g of triethanolamine (0.3 mole) and 33.2 g (0.3 mole) of 1-chloro-2,3-propanediol was introduced into a flask surmounted by a condenser and fitted with a pneumatic agitator and a thermometer.

The mixture was kept at 100° C. for 22 hours.

A dark brown product was obtained and it was washed 5 times by suspension in 50 ml of acetone followed by agitation, decantation and separation of the acetone phase.

After purification in ethanol and drying under vacuum at ambient temperature, 58.3 g of a brown product having the appearance of a lacquer were isolated. This product contained 3.51 g Cl$^-$ ion/kg.

2nd stage: acetylation of tris(2-hydroxyethyl)-(2,3-dihydroxypropyl)ammonium chloride A quatity of 51 g of acetyl chloride was added gradually over 2 hours at ambient temperature and under agitation to 17 g of product obtained in the first stage. Substantial gaseous liberation of hydrochloric acid was observed. The mixture was then heated gradually to 60° C. and this temperature was maintained for 5 hours. The excess acetyl chloride was then removed by evaporation at 80° C. under reduced pressure.

The evaporation residue took the form of a very hard, brown lacquer. 170 ml of tetrahydrofuran were then added to this residue and the mixture boiled for 15 minutes. After cooling, the tetrahydrofuran phase was separated and the operation then repeated. The product took the form of a very viscous coloured liquid. After removal of the tetrahydrofuran by evaporation under vacuum in a rotary evaporator, 20.8 g of a very viscous colourless lacquer were obtained.

The Cl$^-$ ion determination corresponded to 99.7% of the theoretical value calculated for the molecule of tris(2-acetoxyethyl)-(2,3-diacetoxypropyl)-ammonium chloride. The determination of the acetoxy groups by saponification corresponded to 98% of the theoretical value.

EXAMPLE 3

Preparation of n-butyl-tris(2,3-diacetoxypropyl)-ammonium chloride

Preliminary stage: preparation of bis(2,3-dihydroxypropyl)-n-butylamine.

A quantity of 44 g (0.6 mole) of n-butylamine was added to a solution of 53 g (1.32 mole) of sodium hydroxide in 600 ml of ethanol. 166 g (1.5 moles) of 1-chloro-2,3-propanediol were added to this solution cooled to 15° C. and the mixture was left to stand overnight. The sodium chloride formed was then filtered and the ethanol evaporated at 50° C. and under 2 kPa. The weight of the liquid residue composed of crude bis(2,3-dihydroxypropyl)-n-butylamine was 161.4 g.

1st stage: preparation of n-butyl-tris(2,3-dihydroxypropyl)-ammonium chloride

A fresh quantity of 66.3 g (0.6 mole) of 1-chloro-2,3-propanediol was added to the unpurified bis(2,3-dihydroxypropyl)-n-butylamine. These reagents were then brought to a temperature of 100° C. for 26 hours. Separation of the ammonium salt form was carried out in a methanolic medium with the aid of a cation exchange resin (Bio-Rad AG 50W-X8). In this way, 21.9 g of n-butyl-tris(2,3-dihydroxypropyl)ammonium chloride were obtained.

2nd stage: acetylation of n-butyl-tris(2,3-dihydroxypropyl)-ammonium chloride

A quantity of 30.9 g (0.4 mole) of acetylchloride was added to the solid obtained in the previous stage. The resulting mixture was kept under reflux for 5 hours, that is, the time required for the liberation of 95% of the theoretical quantity of hydrochloride acid. The product was then dried under vacuum overnight (25° C.—133 Pa) then recrystallised with a mixture of tetrahydrofuran and ethylether (volume ratio THF/ether=4:6) before being dried a second time at 70° C. and under 133 Pa. In this way, 3.6 g of n-butyl-tris(2,3-diacetoxypropyl)-ammonium chloride with a purity of more than 95% were obtained.

EXAMPLE 4

Preparation of methyl-tris(2-octyloxyethyl)-ammonium chloride

1st stage: preparation of tris(2-octyloxyethyl)-amine

A quantity of 310 g (1.87 moles) of octanoyl chloride were added to a quantity of 92.9 g (0.62 mole) of triethanolamine. The mixture was kept at 110° C. for 7 hours during which time 1.05 moles of hydrochloric acid were liberated. The tris(2-octyloxyethyl)-amine chlorohydrate formed was neutralised with an equivalent quantity of sodium hydroxide in solution in methanol. The sodium chloride residue was then filtered and the filtrate evaporated at 50° C. under a pressure of 2 kPa. In this way, 295 g of tris(2-octyloxyethyl)-amine were collected.

2nd stage: quaternisation of the tris(2-octyloxyethyl)-amine

A quantity of 120 g of tris(2-octyloxyethyl)-amine was treated with 80.8 g (1.6 moles) of methyl chloride at 90° C. in an autoclave in the presence of 150 of acetonitrile as a solvent. After 20 hours reaction, the mixture was evaporated at 50° C. under a pressure of 2 kPa. 114 g of brown solid were obtained, which solid was washed several times with petroleum ether (40–60 fraction). After drying, 56.8 g of methyl-tris(2-octyloxyethyl)-ammonium chloride with a purity of more than 98% were obtained.

We claim:

1. Organic quaternary ammonium compounds, characterised in that they have the general formula:

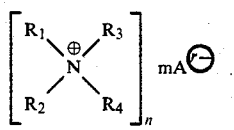

in which,

R$_1$ represents an alkyl, aryl, aryl alkyl or alkyl aryl group, unsubstituted or substituted by at least two ester groups;

R$_2$, R$_3$ or R$_4$ represent alkyl, aryl, aryl alkyl or alkyl aryl groups, each substituted by at least one ester group having the formula:

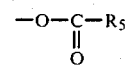

in which

R$_5$ represents an alkyl, aryl, aryl alkyl or alkyl aryl group comprising 1 to 9 carbon atoms;

A 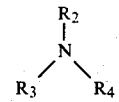 represents an organic or inorganic anion;

n and r are whole numbers;

m is a whole number with the value 1, 2 or 3 and such that the product $m \times r = n$.

2. Compounds according to claim 1, characterised in that at least one of the ester groups is a straight-chain or branched aliphatic ester group in which the R$_5$ group comprises 7 to 9 carbon atoms.

3. Compounds according to claim 1, characterised in that at least one of the ester groups is a straight-chain or branched aliphatic ester group in which the R$_5$ group comprises less than 7 carbon atoms.

4. Compounds according to claim 3, characterised in that at least one of the ester groups is an acetic ester group.

5. Compounds according to claim 4, characterised in that they are methyl-tris(2-acetoxyethyl)-ammonium salts.

6. Compounds according to claim 5, characterised in that they are methosulfate, dodecylsulphate, dodecylbenzenesulphonate and methyl-tris(2-acetoxyethyl)-ammonium chloride.

7. Compounds according to claim 4, characterised in that they are composed of tris(2-acetoxyethyl)-(2,3-diacetoxypropyl)-ammonium chloride and n-butyl-tris(2,3-diacetoxypropyl)-ammonium chloride.

8. A process for preparing the compounds of claim 1, comprising (a) obtaining a tertiary amine of the formula $$\begin{array}{c} R_2 \\ | \\ N \\ / \ \backslash \\ R_3 \quad R_4 \end{array}$$

wherein

R$_2$, R$_3$ and R$_4$ are selected from the group consisting of alkyl, aryl, alkylaryl and arylalkyl, and each R$_2$, R$_3$ and R$_4$ is substituted with at least one OH group;

(b) admixing thereto an alkylating or arylating agent selected from the group consisting of unsubstituted alkyl, aryl, alkylaryl and arylalkyl salts, and alkyl, aryl, alkylaryl and arylalkyl salts substituted with at least two OH groups, in an amount and under reaction conditions effective to obtain a quaternary ammonium salt of the tertiary amine; and (c) admixing thereto an acylating agent selected from the group consisting of (C$_1$–C$_9$) acyl anhydrides and acyl chlorides in an amount and under reaction conditions effective to attain the acylation of at least two OH groups of the tertiary amine.

9. The process of claim 8, wherein the tertiary amine is selected from the group consisting of triethanolamine,
tris(2,3-dihydroxypropyl)amine,
tris(2-hydroxypropyl)amine,
methyl-bis(2,3-dihydroxypropyl)amine, and
N,N-diethanol aniline.

10. The process of claim 9, wherein the tertiary amine is triethanolamine.

11. The process of claim 8, wherein
the alkylating or arylating agent is selected from the group consisting of alkyl, aryl, alkylaryl and arylalkyl halides and sulfates.

12. The process of claim 11, wherein
the alkylating or arylating agent is selected from the group consisting of
dimethylsulfate,
($C_1$–$C_2$) alkyl or benzyl chlorides, bromides and iodides,
methyldodecylbenzene sulfate,
hydroxyalkyl halides, and
hydroxyaryl halides.

13. The process of claim 8, wherein the acylating agent is selected from the group consisting of
acetic anhydride,
benzoic anhydride,
phthalic anhydride,
acetyl chloride, and
propionyl chloride.

14. The process of claim 8, wherein step (b) is performed prior to step (c).

15. The process of claim 8, wherein step (c) is performed prior to step (b).

16. The process of claim 8, wherein step (c) is performed under reflux.

17. The process of claim 8, wherein step (b) is performed at a temperature between about 40° C. and 100° C.

18. The process of claim 8, wherein step (c) is performed at a temperature of about 60° C.

* * * * *